United States Patent [19]

Ayer

[11] Patent Number: 4,567,000

[45] Date of Patent: Jan. 28, 1986

[54] 11-DIFLUOROMETHYLENE STEROIDS

[75] Inventor: Donald E. Ayer, Kalamazoo, Mich.

[73] Assignee: The Upjohn Company, Kalamazoo, Mich.

[21] Appl. No.: 646,605

[22] Filed: Aug. 31, 1984

[51] Int. Cl.[4] .................................................. C07J 1/00
[52] U.S. Cl. .............................. 260/397.3; 260/397.45
[58] Field of Search .......................... 260/397.3, 397.45

[56] References Cited

U.S. PATENT DOCUMENTS

| | | | |
|---|---|---|---|
| 3,450,720 | 6/1969 | Lamcette | 260/397 |
| 3,457,285 | 7/1969 | Board | 260/397.45 |
| 3,504,002 | 3/1970 | Boswell | 260/397.3 |
| 3,705,182 | 12/1972 | Edwards | 260/397.4 |
| 3,927,046 | 12/1975 | van den Broek | 260/397.3 |
| 4,277,468 | 7/1981 | Hofmeister et al. | 260/397.45 |
| 4,292,251 | 9/1981 | Overbeek | 260/397.3 |

OTHER PUBLICATIONS

M. Obayashi et al., Tetrahedron Letters, 23, 2323 (1982).

*Primary Examiner*—Elbert L. Roberts
*Attorney, Agent, or Firm*—Bruce Stein

[57] ABSTRACT

11-Difluoromethylene steroids having progestational and anti-progestational properties, useful as anti-fertility agents, are disclosed as well as a process for making the 11-difluoromethylene steroids.

24 Claims, No Drawings

11-DIFLUOROMETHYLENE STEROIDS

BACKGROUND OF THE INVENTION

Steroids substituted in the $C_{11}$ position with an unsaturated substituent are known. U.S. Pat. No. 3,927,046 discloses 11-methylene and 11-(alkyl substituted)methylene steroids, U.S. Pat. No. 4,292,251 discloses 11β-substituted unsaturated aliphatic hydrocarbon substituents containing 2–3 carbon atoms. Neither of these patents discloses any halogen substitution.

Difluoromethyl steroids are known with the difluoro substituent at $C_{11}$, see U.S. patent application Ser. No. 639,285, filed Aug. 8, 1984 for which the issue fee has been paid.

Steroids containing a fluoromethylene group (=CHF) are known. (E)-11-fluoromethylene and (Z)-11-fluoromethylene steroids are known, see U.S. patent application Ser. No. 639,285, filed Aug. 8, 1984 for which the issue fee has been paid.

Difluoromethylene steroids are known with the difluoromethylene substituent at $C_3$ (U.S. Pat. No. 3,450,720), $C_6$ (U.S. Pat. No. 3,504,002), $C_{16}$ (U.S. Pat. No. 3,705,182) and $C_{16}$ and $C_{17}$ (U.S. Pat. No. 3,457,285). None of these references has the difluoromethylene substituent at $C_{11}$ or even near it.

M. Obayashi et al. in Tetrahedron Letters 23, 2323 (1982) describe a process to prepare (diethylphosphinyl)difluoromethyllithium by reacting diethyl difluoromethylphosphonate and lithium diisopropylamide in THF at −78°. The (diethylphosphinyl)difluoromethyllithium was reacted with ketones producing difluoromethylene compounds. None of the ketones used were steroids or even polycyclic or sterically-hindered as are the protected 11-keto steroids (III) of the present invention. The yields obtained by Obayashi were in the range of 54 to 75%; it is surprising and unexpected that the sterically-hindered (11-difluoromethylene steroids (IV) are obtained in yields of 70–80%.

SUMMARY OF THE INVENTION

Disclosed is a 11-difluoromethylene steroid (V).

Also disclosed is a $\Delta^4$-3-keto-17-substituted-11-difluoromethylene steroid (XV).

Further disclosed are the syn- and anti-isomers of an oxime of formula (XVI).

DETAILED DESCRIPTION OF THE INVENTION

The 11-hydroxy-19-norandrostenediones (I) are known to those skilled in the art or can be readily prepared from known steriods by methods well known to those skilled in the art. The 11-hydroxy-19-norandrostenediones (I) are oxidized to the corresponding 11-keto-19-norandrostenedione (II) by methods well known to those skilled in the art using such reagents as chromium trioxide, N-bromoacetamide in pyridine or lead tetraacetate, see Steroid Reactions, edited by C. Djerassi, Holden-Day, Inc., San Francisco, 1963, Chapter 2. Either 11α- or 11β-hydroxy steroids may be used as both produce the same 11-keto compound (II).

The 11-keto-19-norandrostenediones (II) are 3,11,17-triones and therefore preferably have the 3 and 17-keto functionality protected prior to further reaction at $C_{11}$. The selective protection of carbonyl groups is well known to those skilled in the art, see Steroid Reactions, supra, Chapter 1. It is preferred that the 3 and 17-keto functionality be protected as the 3,17-bisethylene glycol ketal to produce the protected 11-keto steroid (III).

The protected 11-keto steroids (III) are converted to the protected 11-difluoromethylene steroids (IV) by reaction with (diethylphosphinyl)difluoromethyl lithium. A solution of the protected 11-keto steroid (III) in an inert solvent such as THF, dioxane, ethylene glycol dimethyl ether or the like is added to a cold solution of (diethylphosphinyl)difluoromethyllithium at about −60° to about −80°. This reagent may conveniently be prepared by treatment of diethyl difluoromethylphosphonate with 1.1 equivalents of lithium diisopropylamide in THF at −78° [See Tetrahedron Letters 23, 2323 (1982)]. The reaction mixture is maintained at about −60° for several hours and then is allowed to warm slowly to 20°–25° and stand overnight. Volatile constituents are evaporated under reduced pressure and the residue is partitioned between an appropriate organic solvent such as ether, methylene chloride or ethyl acetate and water. The extract is washed and dried in the usual way. The crude product is purified by chromatography on silica gel and crystallization.

The protected 11-difluoromethylene steroid (IV) has the $C_3$ and $C_{17}$ protecting groups removed to produce the key intermediate 11-difluoromethylene steroid (V) by hydrolysis under acidic conditions. A solution of the protected 11-difluoromethylene steroid (IV) in an appropriate solvent such as aqueous acetone or aqueous methanol is acidified with an inorganic acid (such as hydrochloric, sulfuric or phosphoric acid) or an organic acid (such as acetic, trifluoroacetic, p-toluene sulfonic acid). The solution is allowed to stand, preferably at 20°–25°, until hydrolysis is complete (TLC), then the reaction mixture is worked up by conventional means to give the 11-difluoromethylene steroid (V).

The 11-difluoromethylene steroid (V) is transformed to the pharmacologically useful 17-substituted-11-difluoromethylene steroid (VIII) by a Grignard reaction with the 17-keto group. First the $C_3$-ketone must be protected.

Prior to converting the 17-keto group to the desired 17β-hydroxy-17α-substituent, the 3-keto group must be protected. It can be protected as an enol ether, enamine, ketal or thio ketal as is well known to those skilled in the art. See, Steroid Reactions, supra, Chapter 1. The thioketal and enamine protecting groups form selectively at $C_3$ and are preferred. Especially preferred are ethanedithiol ketals and pyrrolidine enamines.

The $C_3$ protected 11-difluoromethylene steroids (VI) are then allowed to react with the appropriate reagent, as is well known to those skilled in the art, to produce the corresponding protected 17α-substituted-11-difluoromethylene steroids (VII). For example, to produce 17β-hydroxy-17α-propynyl steroids (VII) where $R_{17\alpha}$ is an alkynyl group such as propynyl (—C≡C—CH$_3$), the $C_3$ protected 11-difluoromethylene steroid (VI) is allowed to react with the appropriate Grignard reagent as is well known in the art, see Example 8. To produce 17α-ethynyl-17β-hydroxy-11-difluoromethylene steroids (VII) where $R_{17\alpha}$ is an ethynyl group the $C_3$ protected 11-difluoromethylene steroids (VI) are allowed to react with acetylene in the usual manner. Similarly the 17-ketones can be allowed to react with methyl Grignard reagent and other lower alkyl and lower alkenyl Grignard reagents to afford the 17α-methyl, lower alkyl and lower alkenyl derivatives. The 17-ketones can also be reduced with agents such as sodium borohydride (in alcohol at 0°) to give the 17β-hydroxy-11-difluoromethylene steroids (VII) where $R_{17}\alpha$ is a hydrogen atom.

The protected 17α-substituted-11-difluoromethylene steroids (VII) are transformed to the 17α-substituted-11-difluoromethylene steroid (VIII) by hydrolysis. The thioketal protecting group at $C_3$ may be hydrolyzed from the 17α-substituted-11-difluoromethylene steroids (VII) to produce the corresponding $\Delta^4$-3-keto-17α-substituted-11-difluoromethylene steroids (VIII) by reaction with methyl iodide, water and acetone (preferably in a closed reactor at 30°–40° for several days). The 17α-substituted steroids protected at $C_3$ by an enamine (VII) are usually hydrolyzed without prior purification by treatment of the Grignard reaction mixture with a base (such as sodium hydroxide in aqueous methanol, see Example 8) to produce the corresponding $\Delta^4$-3-keto-17α-substituted-11-difluoromethylene steroids (VIII).

The 17α-substituted-11-difluoromethylene steroid (VIII) is a 17β-hydroxy steroid. Chart C discloses the necessary reactions to transform the 17β-hydroxy group of the 17α-substituted-11-difluoromethylene steroid (VIII) to the corresponding ether (X) or ester (XI). The ethers (X) and esters (XI) are prepared by methods well known to those skilled in the art. Thus the 17β-hydroxy group is esterified with the appropriate acid anhydride or acid chloride in pyridine (preferably in the presence of 4-dimethylaminopyridine) to give the ester (XI).

The $\Delta^4$-3-keto-17β-hydroxy functionality of the 17α-substituted-11-difluoromethylene steroid (VIII) is first converted to the 3-ketal (IX) prior to etherification. The 3-ketal (IX), prepared by the reaction of the $\Delta^4$-3-keto group with ethylene glycol by standard methods is allowed to react with sodium hydride in an appropriate solvent such as DMF or THF. An alkylating agent, such as methyl iodide, is then added and the reaction mixture is agitated at 20°–25° until etherification is complete. The resultant 3-ketal-17β-alkoxy steroids are hydrolyzed under standard conditions to give the 17-ether (X). Alternatively the thioketal intermediate (VII) can be etherified and then the thioketal hydrolyzed as described to give the 17-ether (X).

The desired $\Delta^4$-3-keto-17-substituted-11-difluoromethylene steroid (XV) can also be obtained (Chart D) from the corresponding 17-substituted-11-keto steroid (XII) where the transformation at $C_{17}$ is effectuated prior to the introduction of the difluoromethylene group at $C_{11}$. First, the 17-substituted-11-keto steroid (XII) is protected at $C_3$ by reaction with ethylene glycol in the presence of an acid catalyst such as p-TSA in an appropriate solvent such as toluene, with azeotropic removal of water to give the protected 17-substituted-11-keto steroid (XIII). Alternatively the protected 17-substituted-11-keto steroid (XIII) can be obtained from the reaction of the 17-substituted-11-keto steroid (XII) with ethylene glycol, trimethylorthoformate and p-TSA at 25°. Introduction of the 11-difluoromethylene group, as discussed supra, gives the ketal protected 17-substituted-11-difluoromethylene steroid (XIV); removal of the 3-ketal of (XIV) gives the $\Delta^4$-3-keto-17-substituted-11-difluoromethylene steroid (XV).

The $\Delta^4$-3-keto-17-substituted-11-difluoromethylene steroid (XV) can be transformed to the corresponding oxime (XVI) by reaction with hydroxylamine or an alkyl derivative of hydroxylamine, preferably methylhydroxyl amine, in a suitable solvent such as ethanol, as is well known in the art. Both the syn- and anti-isomers are produced.

The 11-difluoromethylene (V) steroids are intermediates useful in the production of the pharmacologically active 17-substituted-11-difluoromethylene steroids (VIII, X, XI, XV and XVI).

The $\Delta^4$-3-keto-17-substituted-11-difluoromethylene steroid (XV) encompasses the 17α-substituted-11-difluoromethylene steroids (VIII, $R_{17}\beta$ is a hydrogen atom), the ethers (X, $R_{17}\beta$ is alkyl of 1 thru 4 carbon atoms), and the esters (XI, $R_{17}\beta$ is —CO—$R_{17}$C).

The 11-difluoromethylene steroids (VIII, X, XI, XV and XVI) have progestational, antiprogestational and male and female antifertility activity and therefore are useful for pregnancy salvage and menopausal therapy and as male and female contraceptive agents in humans and other mammals.

The 11-difluoromethylene steroids (VIII, X, XI, XV and XVI) may be used either individually or in combination with each other.

The 11-difluoromethylene steroids (VIII, X, XI, XV and XVI) which have female progestational activity are useful in treating pregnancy salvage and menopausal therapy and are those steroids which have similar activity to progesterone in the following tests: DAO (diamine oxidase), McPhail, pregnancy maintenance in castrated laboratory animals as is well known to those skilled in the art, see for DAO Assay, A New Progestational Assay; Uterine Diamine Oxidase, Fertility and Sterility 1976 by M. E. Harris and K. S. Kim; Uterine Diamine Oxidase, a Marker for Progestin Action, by C. H. Spilman, D. C. Beuving and K. K. Bergstrom, *Reproductive Processes and Contraception*, (edited by K. W. Harris), Plenium Publishing Corp., New York 1981, p. 509–519; for McPhail Assay, J. Physiol. 83, 145 (1935); and for pregnancy maintenance, Proc. Soc. Exper. Biol. & Med. 99, 500 (1958); Recent Progress in Endocrinology by Reproduction by F. J. Saunders and R. L. Elton, Academic Press, 1959, p. 227–254. The 11-difluoromethylene steroids (VIII, X, XI, XV and XVI) useful for treating pregnancy salvage or in menopausal therapy are administered so that the female mammal receives about 0.002 to about 0.50 mg/kg/day or for a 50 kg female, the amount would be about 0.1 to about 25 mg/day, preferably from about 1 to about 5 mg/day.

The 11-difluoromethylene steroids (VIII, X, XI, XV and XVI) which have progestational or antiprogestational activity are useful as male and female contraceptive agents and are used to provide reversible contraception for male and female mammals post-puberty which are selected from the group consisting of man, male dog, tom, bull, stallion, ram, boar, male rat and male mouse and their female counterparts.

With regards to the human, there are many intances in which the female cannot take various types of chemical contraceptive agents and does not or cannot use various physical contraceptive devices such as IUD (IUCD) or diaphragm. In addition, many women do not wish to rely on non-prescription (over-the-counter) foams, gels and cream chemical contraceptive agents. Therefore, there are numerous instances in which it would be highly desirable to have a reliable reversible contraceptive agent for men. This is particularly true in view of the fact that the only reversible contraceptive agent for man is a mechanical device (prophylactic) which has the distinct disadvantage of low efficacy. In addition, there is the disadvantage of mechanical devices of having to interrupt intercourse to properly position the device.

The useful warm blooded animals can be divided into two groups—domesticated (dog, tom) and commercial (bull, stallion, ram and boar). The domesticated male animals usually cohabitate with the females. The commercial male animals are usually separated from the females because either it is desired that the particular males not fertilize the females so that artificial insemination may be used, or even if the particular males are well suited to fertilizing the females it may be desired that they do so at the present time. The use of the methods of the present invention permits one to allow both the domestic and commercial male and females to cohabitate without sterilization of either sex and without unwanted pregnancies and still retain the flexibility of fertilizing the female when desired either with a desired male or by artificial insemination.

With regards to the rodents, the rat and mouse, it is highly desirable of course to be able to eradicate or control the populations of these rodents with the methods of the present invention. These rodents can be controlled and/or eradicated by decreasing the fertility of these rodents by use of the methods of the present invention. This of course would not eliminate the rodents which are present, but only future rodents which these animals might conceive, thereby decreasing future populations of these undesirable animals.

The 11-difluoromethylene steroids (VIII, X, XI, XV and XVI) which are useful as male contraceptive agents are those which depress gonadotropins in castrated laboratory animals. See, Fed. Proc. 18, 1057 (1959). The 11-difluoromethylene steroids (VIII, X, XI, XV and XVI) are administered such that the male mammal receives about 0.01 to about 1.0 mg/kg/day. For a 70 kg male, the amount would be about 0.7 to about 70 mg/day.

The 11-difluoromethylene steroids (VIII, X, XI, XV and XVI) useful as female contraceptive agents are those with anti-progestational activity, i.e., those compounds which inhibit the action of progesterone in the following tests: DAO, nuclear translocation, expression of uteroglobin gene, and most importantly interruption of pregnancy in laboratory animals as is well known to those skilled in the art, see for DAO assay supra. The female contraceptive steroids are administered such that the female mammal receives about 0.01 to about 1.0 mg/kg/day. For a 50 kg female, the amount would be about 0.5 to about 50 mg/day.

The exact dose of the 11-difluoromethylene steroids (VIII, X, XI, XV and XVI) will depend on the particular compound, the weight, age, and physical condition of the particular patient to be treated.

The 11-difluoromethylene steroids (VIII, X, XI, XV and XVI) are administered by oral, or parenteral, in sustained release form, by intrauterine, or by intravaginal means in the appropriate dosage forms.

Oral dosage forms include both solid and liquid. The solid dosage forms include tablets (compressed, tablet triturates, enteric coated, sugar coated, film coated and multiple compressed), capsules (hard and soft gelatin), treats, bait, veterinary premix and animal feed. The liquid oral dosage forms include, for example, aqueous solutions (elixirs and syrups), emulsions, and suspensions. In the parenteral sustained release form, the active ingredient is slowly released over a prolonged period as is well known to those skilled in the art. These preparations are known as sustained release parenteral forms or depo forms.

One method of formulating parenteral depo compositions is to administer the drup dissolved in or suspended in oil. An oleaginous solution or suspension injected intramuscularly provides a depot which slowly releases the drug to tissue fluid and the blood. The oil may be modified by the inclusion of wax or some other water-repellant substance such as aluminum stearate which further reduces the release rate of the therapeutically active ingredient.

An alternative long acting parenteral composition is one where the relatively water-insoluble steroids are suspended in an aqueous medium. The aqueous medium can be modified by the addition of certain hydrocolloids such as gelatin, carboxymethyl cellulose or polyvinylpyrrolidone. The contraceptive steroids of the present invention are quite water-insoluble and those which are crystalline lend themselves very well to this type of formulation.

Long acting parenteral steroidal compositions in oil are well known to those skilled in the art. For example, see testosterone cypionate USP (See Physicians Desk Reference, PDR, 31 edition, 1977, page 1625); nandrolone phenpropionate N.F. (PDR, ibid., page 1138); estradiol cypionate injection USP and testosterone enanthate USP (PDR, ibid., page 1512) which is advertised as having a duration of action of about 4 weeks.

Long acting aqueous parenteral compositions are also well known to those skilled in the art. See British Pat. Nos. 705,343 and 731,933. Various long acting aqueous parenteral steroidal preparations are well known to those skilled in the art. See British Pat. No. 731,933, Examples 1–4 and methylprednisolone acetate suspension N.F. (PDR, ibid., page 1623) and medroxyprogesterone acetate suspension (PDR, ibid., page 1625).

U.S. Pat. No. 4,038,389 discloses and claims aqueous parenteral compositions containing 200–600 mg/ml of medroxyprogesterone. The usual therapeutic dose of medroxyprogesterone is 2.5–10 mg, see PDR, ibid., page 1648, where the product is marked in oral tablet form at two dose levels, 2.5 and 10.0 mg. The very high dose of medroxyprogesterone disclosed in U.S. Pat. No. 4,038,389 is obviously because it is in long acting (depot) form intended to have a duration of action of many weeks. See The Journal of Reproductive Physiology 13, 113 (1974), where the composition claimed in U.S. Pat. No. 4,038,389 had a duration of action of at least 3 months in preventing pregnancy.

In 1977 five papers appeared in the journal Contraception, Vol. 15, at pages 627, 635, 649, 669 and 679, which show that testosterone can be administered parenterally in a form which will provide effective amounts of testosterone for a period of at least one month.

Therefore, the technology is known to those skilled in the art to formulate the steroids of the present invention into depot or long acting parenteral preparations. The depot parenteral preparations should release the male contaceptive steroid at the rate of about 0.01 to about 1.0 mg/kg/day.

An alternative pharmaceutical composition to deliver the contraceptive steroids to the desired animal at a controlled rate over a long period of time is the implant. The technology for formulating the proper implants is well known to those skilled in the art. The J. of Animal Science 35, 251 (1972), in an article by M. L. Ogilvie, describes a polyurethane implant containing melengesterol acetate which was used in heifers for over four months. John B. Herrick in Animal Nutrition and Health, April 1977, at page 23, describes a number of growth promotants for beef cattle. Many of these growth promotants are steroids, including testosterone, and are administered by implants. L. L. Ewing et al., in Contraception 13, 583 (1976), describes a method of decreasing sperm counts in male rhesus monkeys by administering testosterone via subdermal dimethylpolysiloxane implants. The implants were left in for 70 days, and the results demonstrate the satisfactory nature of this method. W. E. Johansson et al., in Contraception 13, 287 (1976), describes using dimethylpolysiloxane implants containing a steroid in women for over four months. Further, U.S. Pat. No. 3,896,819 discloses a drug delivery device for administering a drug at a controlled rate for a prolonged period of time. The drug delivery device can be used as an implant, see column 6, starting at line 55. This implant is useful with steroids such as methyltestosterone, see column 19, starting at line 24. The implant should release the contraceptive steroids of the present invention at the rate of about 0.01 to about 1.0 mg/kg/day.

The pharmaceutically therapeutically active contraceptive steroids of the present invention are administered orally or parenterally in unit-dosage forms or multiple-dosage forms. Unit-dose forms refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampuls and syringes (parenteral) and individually packaged tablet or capsule (oral-solid). Unit-dose forms may be administered in fractions or multiples thereof. A multiple-dose form is a plurality of identical unit-dose forms packaged in a single container to be administered in segregated unit-dose form. Examples of multiple-dose forms include vials (parenteral) and bottles of tablets of capsules (oral-solid). Hence, multiple dose forms is a multiple of unit-doses which are not segregated in packaging. The specifications for the unit-dosage form and the multiple-dosage form are dictated by and directly dependent on (a) the unique characteristics of the particular steroid and the particular therapeutic effect to be achieved and (b) the limitations inherent in the art of compounding such a therapeutically active compound for reversible contraception.

The individual oral solid pharmaceutical dosage forms, tablets and capsules, are packaged individually (unit dose) or in quantity (multiple dose containers), for examples bottles of 50, 100, 500, 1,000 or 5,000. The exact amount of the particular steroid per dosage unit (tablet or capsule) is adjusted so that the tablet or capsule, a fraction or multiple thereof, provides the patient with an effective amount. It is preferred that each tablet or capsule contain 1–250 mg of the steroids. The exact dosage depends on the particular compound, the age, weight, physical condition and particular patient or animal, as is known to those skilled in the art. Tablets and capsules are given in sufficient number and frequency to obtain the desired contraceptive effect.

U.S. Pat. No. 4,252,798 describes various dosage forms useful for a male contraceptive agent. While that patent describes dosage forms useful for a male contraceptive agent, those forms are equally applicable to the female contraceptive steroids of the present invention. U.S. Pat. No. 4,252,798 has a thorough discussion of sustained release tablets and capsules, tablet formulations used to treat dogs, cats and rabbits, treats, bait, liquid dosage forms, veterinary premixes, and animal feed compositions.

Following cessation of administration of the steroids of the present invention, or at the end of the metering out of the parenteral sustained release formulation, contraception will be maintained only for a very short period, and gradually, the animal's ability to fertilize or be fertilized returns to normal.

The steroids of the present invention are also useful for treating benign prostatic hypertrophy (BPH) in humans. The steroids are administered in the dosage forms described above and in the dosages previously described.

Biological information in the form of progesterone receptor relative binding affinity data determined according to the procedure of D. Philibert et al, Endocrinology 101, 1850 (1977) set forth in TABLE 1.

DEFINITIONS

The definitions and explanations below are for the terms as used throughout the entire patent application including both the specification and the claims.

All temperatures are in degrees Centigrade.

TLC refers to thin-layer chromatography.

THF refers to tetrahydrofuran.

DMF refers to dimethylformamide.

SSB refers to an isomeric mixture of hexanes.

p-TSA refers to p-toluenesulfonic acid monohydrate.

Saline refers to an aqueous saturated sodium chloride solution.

IR refers to infrared spectroscopy.

UV refers to ultraviolet spectroscopy.

CMR refers to C-13 magnetic resonance spectroscopy, chemical shifts are reported in ppm ($\delta$) downfield from TMS.

NMR refers to nuclear (proton) magnetic resonance spectroscopy, chemical shifts are reported in ppm ($\delta$) downfield from TMS.

TMS refers to tetramethylsilane.

$[\alpha]_D^{25}$ refers to the angle of rotation of plane polarized light (specific optical rotation) at 25° with the sodium D line (5893A).

MS refers to mass spectrometry expressed as m/e or mass/change unit.

When solvent pairs are used, the ratios of solvents used are volume/volume (v/v).

R is hydroxy or alkoxy where the alkyl group is from 1 thru 4 carbon atoms.

$R_3$ is alkyl of 1 thru 5 carbon atoms with the proviso that the $R_3$ groups can be the same or different and they can be connected and when connected, may be connected to an oxygen or nitrogen atom.

$R_6$ is a hydrogen atom or methyl group with the proviso that when $R_6$ is a methyl group, $R_7$ is a hydrogen atom.

$R_7$ is a hydrogen atom or methyl group with the proviso that when $R_7$ is a methyl group, $R_6$ is a hydrogen atom.

$R_{16}$ is a hydrogen atom or methyl or ethyl group.

$R_{17A}$ is a hydrogen atom, methyl or ethyl group or trifluoromethyl group.

$R_{17\alpha}$ is a hydrogen atom, alkyl of 1 thru 4 carbon atoms, —C≡C— $R_{17}A$ or —CH=CH—$R_{17}B$.

$R_{17B}$ is a hydrogen atom, methyl or ethyl group or —CH=CH$_2$ group.

$R_{17\beta}$ is alkyl of 1 thru 4 carbon atoms and —CO—$R_{17C}$.

$R_{17\beta'}$ is alkyl of 1 thru 4 carbon atoms.

$R_{17C}$ is alkyl of 1 through 6 carbon atoms, and phenyl.

$R_{18}$ is a methyl or ethyl group.

$R_{31}$ is alkyl of 1 thru 4 carbon atoms.

~ indicates that the attached group can be in either the α or β configuration.

. . . . is a single or double bond.

When the term "alkyl of ____ thru ____ carbon atoms" is used, it means and includes isomers thereof where such exist.

Ether refers to diethyl ether.

Z is —N—(R$_3$)$_2$, —SCH$_2$CH$_2$S—, —OCH$_2$CH$_2$O— or —OR$_{31}$.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

Estr-4-ene-3,11,17-trione (II)

To a degassed stirred solution of 11α-hydroxy-19-norandrostenedione (I) in acetic acid (225 ml) is added in order a solution of manganese sulfate (2.25 g) in water (130 ml), a solution of chromium trioxide (15 g) in water (15 ml) and concentrated sulfuric acid (14 ml). The sulfuric acid is added dropwise (over 15 min) keeping the temperature near 15° by cooling in an ice bath. The cooling bath is removed after 1.5 hours when TLC shows the reaction to be complete. The mixture is cooled to 15° and sodium hydroxide (50%, 124 ml) diluted with water (147 ml) is added dropwise. Finally a solution of sodium bisulfite in water (7.7 g in 67.5 ml) is added. The precipitate is filtered, washed well with water and dried under reduced pressure to give the title compound, mp 204°–209°; UV (ethyl alcohol) $\lambda_{max}$=239 nm ($\epsilon$=16,000); IR (mull) 1742, 1711, 1674 and 1617 cm$^{-1}$; MS (m/e)=286, 268, 258 and 244; NMR (CDCl$_3$)=0.89 and 5.85 δ.

PREPARATION 2

Estr-5-ene-3,11,17-trione 3,17-bisethylene glycol ketal (III)

A mixture of estr-4-ene-3,11,17-trione (II, Preparation 1, 41 g) in methylene chloride (543 ml), ethylene glycol (308 ml), triethylortho formate (138 ml) is degassed followed by the addition of p-TSA (410 mg). The mixture is refluxed for 6 hours. The mixture is cooled and diluted with bicarbonate solution. The methylene chloride layer is separated, washed several times with water, dried and concentrated to a foam. The foam is triturated several times with diethyl ether-SSB and dried to give the title compound, NMR (CDCl$_3$) 0.85, 3.50 and 5.43 δ; MS (m/e) 374, 356, 346 and 99.

PREPARATION 3

Diethylphosphinyl-difluoromethyllithium

A 5° solution of lithium diisopropylamide in THF (7.7 mmol, 17 ml) is added slowly (10 min) to a solution of diethyl difluoromethylphosphonate (8 mmol, 1.5 g) in THF (20 ml) with dry ice/acetone cooling. The mixture is stirred for 5 min before steroid addition.

EXAMPLE 1

11-Difluoromethylene-estr-5-ene-3,17-dione 3,17-bisethylene glycol ketal (IV)

A solution of estr-5-ene-3,11,17-trione 3,17-bisethylene glycol ketal (III, Preparation 2, 1.5 g) in THF (25 ml) is added slowly to a solution of diethylphosphinyl-difluoromethyllithium (Preparation 3, 7.7 mmol) in THF cooled in dry ice/acetone. The mixture is kept cold (about −60° or less) for an additional 2 hr and then allowed to warm to 20°-25° and let stand overnight. The THF is then removed under reduced pressure to give a solid which is partitioned between methylene chloride and 50% saline. The organic phase is separated, filtered thru sodium sulfate and concentrated to give crude title compound. The crude material is chromatographed using silica gel (200 g) and elution (50 ml franctions) with acetone/methylene chloride (5/95). The appropriate fractions are pooled and concentrated to give the title compound. IR (mull) 1740 cm$^{-1}$; CMR (CDCl$_3$) 150.8, 136.46, 120.31, 118.75, 109.26 and 88.30 δ.

EXAMPLE 2

11-Difluoromethylene-estr-4-ene-3,17-dione (V)

A mixture of 11-difluoromethylene-estr-5-ene-3,17-dione 3,17-bisethylene glycol ketal (IV, Example 1, 0.61 g) in acetone (30 ml) and hydrochloric acid (6N, 0.2 ml) is allowed to stand at 20°-25° for 2.5 hr and is then mixed with potassium bicarbonate (1N, 25 ml). The mixture is concentrated to dryness and then extracted with ether which gives a crystalline residue which is recrystallized from acetone-hexane to give the title compound; mp 158°-164.5°; IR (mull) 1748.4, 1741.7, 1676.1 and 1624.0 cm$^{-1}$; UV (ethyl alcohol) $\lambda_{max}$=238 nm ($\epsilon$=16,700); NMR (CDCl$_3$) 0.92 and 5.9 δ; CMR (CDCl$_3$) 224.5, 206.5, 164.56, 151.07, 125.52 and 87.17 δ; MS (m/e) 320, 305, 278 and 211.

EXAMPLE 3

11-Difluoromethylene-estr-4-ene-3,17-dione 3-pyrrolidine enamine (VI)

A mixture of 11-difluoromethylene-estr-4-ene-3,17-dione (V, Example 2, 0.48 g) in hot methanol (2–3 ml) is mixed with pyrrolidine (0.4 ml). The mixture is chilled and filtered. The filter cake is washed with cold methanol and dried to give the title compound.

EXAMPLE 4

11-Difluoromethylene-17β-hydroxy-17α-(1-propynyl)-estr-4-en-3-one (VIII)

11-Difluoromethylene-estr-4-ene-3,17-dione 3-pyrrolidine enamine (VI, Example 3) is dissolved in propynyl magnesium bromide (0.5M, 5 ml) in THF-ether and allowed to stand for 1 hr. Water (2 ml), methanol (6 ml) and sodium hydroxide (2N, 1 ml) are added and the mixture heated for 1 hr at 45°. The mixture is then cooled, diluted with water and extracted with ether.

The extracts are combined, washed with dilute hydrochloric acid, water, dried over magnesium sulfate and concentrated under reduced pressure to a crystalline residue. Chromatography on silica gel and elution with ethyl acetate/hexane (55/45) gives a solid which is crystallized from acetone-SSB to give the title compound; mp 113°–115°; UV (ethyl alcohol) $\lambda_{max}=239$ nm ($\epsilon=16,650$); IR (mull) 3392, 2231, 1741, 1653 and 1626 cm$^{-1}$; MS (m/e) 360, 345 and 279.

EXAMPLE 5

11-Difluoromethylene-13-ethylgon-5-ene-3,17-dione 3,17-bisethylene glycol ketal (IV)

13-Ethylgon-5-ene-3,11,17-trione 3,17-bisethylene glycol ketal (III, U.S. Pat. No. 4,031,074, 0.71 g) is dried for 16 hr under reduced pressure then dissolved in THF (10 ml) and cooled in a dry ice/acetone bath. A solution of diethylphosphinyl-difluoromethyllithium in THF (Preparation 3, 4 mmol, 20 ml) at $-78°$ is added rapidly. The mixture is permitted to warm to $-10°$ over a period of 6 hr, then permitted to stand overnight. It is worked up as in Example 1, chromatographed on silica gel (100 g), eluted with acetone/methylene chloride (5/95, containing 0.1% pyridine) to give a solid which is crystallized from acetone/methylene chloride to give the title compound; mp 200°–201°; CMR (CDCl$_3$) 150.4, 136.53, 120.32, 119.94, 109.29, 88.10 and 8.45 $\delta$.

EXAMPLE 6

11-Difluoromethylene-13-ethylgon-4-ene-3,17-dione (V)

A mixture of 11-difluoromethylene-13-ethylgon-5-ene-3,17-dione 3,17-bisethylene glycol ketal (IV, Example 5, 053 g) in acetone (30 ml) containing hydrochloric acid (6N, 0.2 ml) is allowed to stand at 20°–25° for 3 hr and then mixed with potassium bicarbonate (1N, 25 ml) and concentrated to a solid. The solid is extracted with ether to give an oil which slowly crystallizes to give the title compound; TLC Rf=0.40, ethyl acetate/hexane (40/60).

EXAMPLE 7

11-Difluoromethylene-13-ethylgon-4-ene-3,17-dione 3-pyrrolidine enamine (VI)

A solution of 11-difluoromethylene-13-ethylene-4-ene-3,17-dione (V, Example 6, 0.44 g) in hot methanol (2 ml) is mixed with pyrrolidine (0.4 ml) giving a heavy precipitate. The mixture is cooled at $-15°$ for 1 hr, then centrifuged. The crystals are mixed with methanol (5 ml) at $-15°$ and recentrifuged. The solid is dried at 40° under reduced pressure to give the title compound.

EXAMPLE 8

11-Difluoromethylene-13-ethyl-17$\beta$-hydroxy-17$\alpha$-(1-propynyl)-gon-4-en-3-one (VIII)

11-Difluoromethylene-13-ethylgon-4-en-3,17-dione 3-pyrrolidine enamine (VI, Example 7) is suspended in propynyl magnesium bromide (5 ml) in THF-ether and stirred for 2 hr. Additional Grignard (5 ml) is added and the mixture stirred for 1 hr. Water (2 ml) and methanol (6 ml) are slowly added. Following additions of sodium hydroxide (1N, 2 ml) and methanol (6 ml) the mixture is stirred at 45±5° for about 2 hr and then concentrated to a small volume. The residue is partitioned between ether and hydrochloric acid (0.5N). The ether extracts are combined, washed with saline (50%), potassium bicarbonate (1N), saline, dried over magnesium sulfate and concentrated to give an oil. The oil is chromatographed on silica gel (75 g) and eluted with ethyl acetate/hexane (30/70) collecting 25 ml fractions. The appropriate fractions (16–25) are pooled and concentrated to give the title compound; NMR (CDCl$_3$) 1.08, 1.88, and 5.9 $\delta$; CMR (CDCl$_3$) 207.4, 165.60, 150.1, 125.41, 88.1, 82.96, 82.18, 80.98, 9.29 and 3.67 $\delta$. This material is crystallized from methanol, mp 167°–168°; IR (mull) 3409.1, 1736.8, 1654.9 and 1619.2 cm$^{-1}$; UV (ethyl alcohol) $\lambda_{max}=239$ nm ($\epsilon=16,700$); MS (m/e) 374, 345 and 293.

CHART A

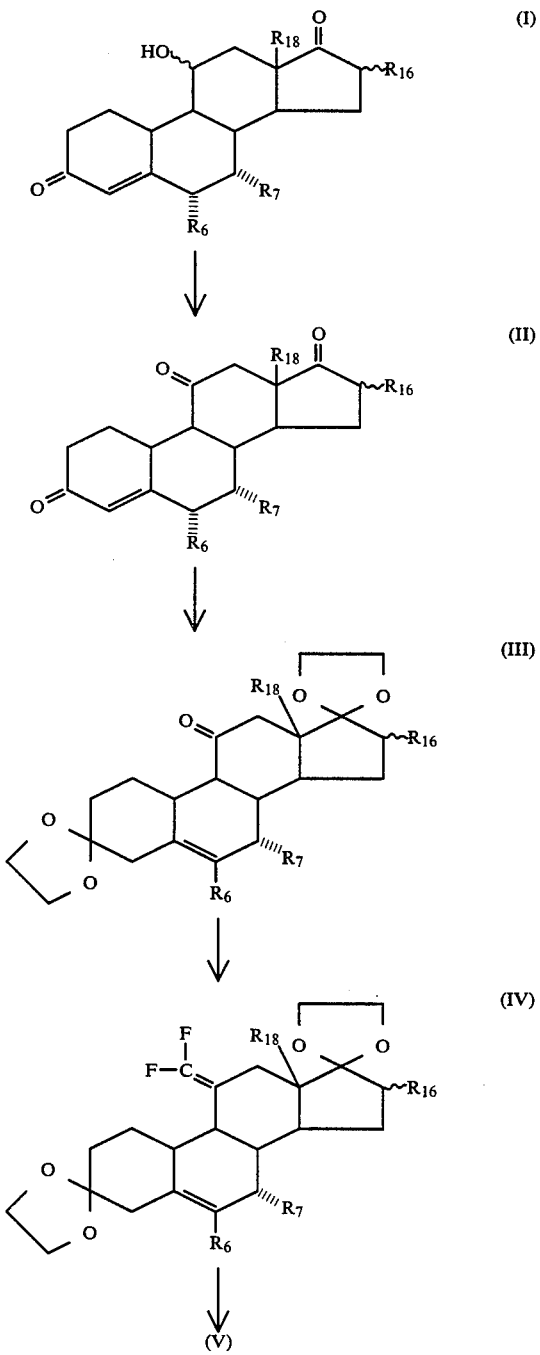

CHART B
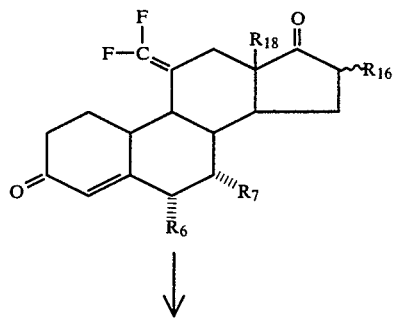
(V)
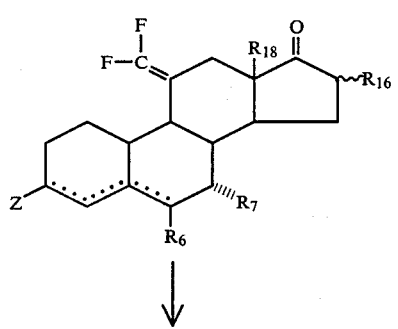
(VI)
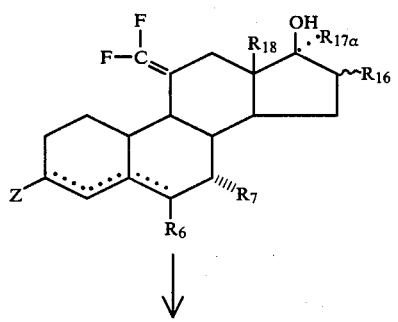
(VII)
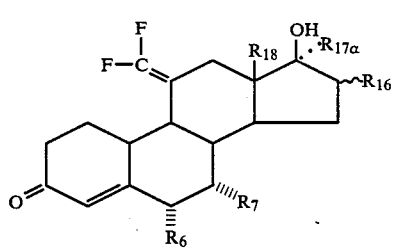
(VIII)
CHART C
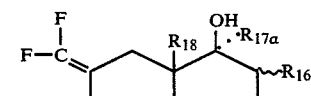
(VIII)
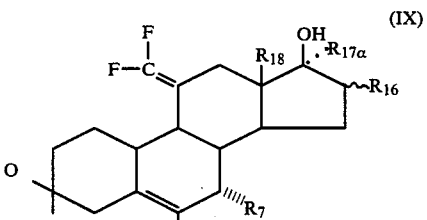
(IX)
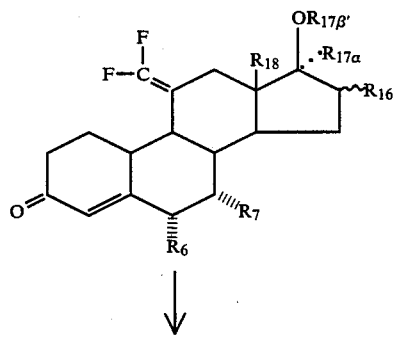
(X)
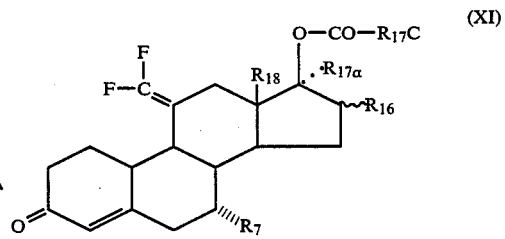
(XI)

CHART D

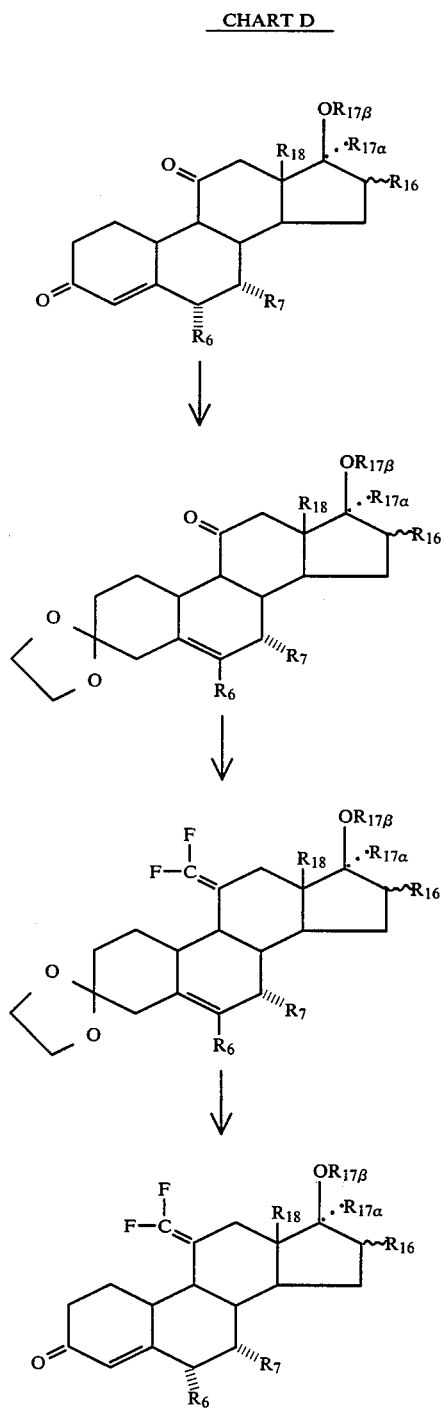

CHART E

-continued
CHART E

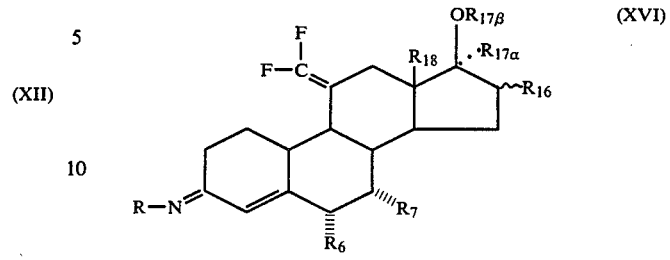

TABLE 1

| Compound | RBA[1] (%) Rabbit | RBA[1] (%) Rat | DAO[2] Dose (μg) | DAO[2] BP |
|---|---|---|---|---|
| 11-Difluoromethylene-17β-hydroxy-17α-(1-propynyl)-estr-4-en-3-one | 82 | 269 | 10 | 117 |
|  |  |  | 50 | 29 |
|  |  |  | 100 | 19 |
|  |  |  | 200 | 15 |
| 11-Difluoromethylene-13-ethyl-17β-hydroxy-17α-(1-propynyl)-gon-4-en-3-one | 104 | Not run | Not run |  |

[1]Relative Binding Affinity, progesterone = 100%
[2]Diamine oxidase; when biopotency (BP) value is 0, the test completely inhibits the progesterone induced DAO. When the value is 100, the test compound does not give any inhibition of progesterone induced DAO enzyme. The lower the value the greater the anti-progestin activity of the test compound.

I claim:
1. A 11-difluoromethylene steroid of the formula

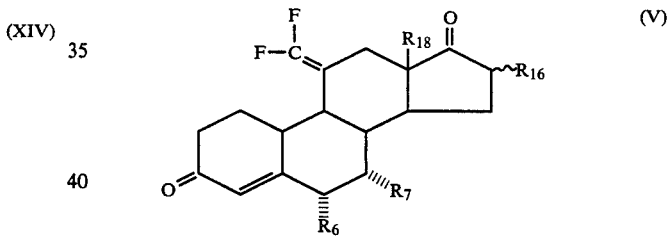

where
$R_6$ is a hydrogen atom or methyl group with the proviso that when $R_6$ is a methyl group, $R_7$ is a hydrogen atom;
$R_7$ is a hydrogen atom or methyl group with the proviso that when $R_7$ is a methyl group, $R_6$ is a hydrogen atom;
$R_{16}$ is a hydrogen atom or methyl or ethyl group;
$R_{18}$ is a methyl or ethyl group; and
∼ indicates that the attached group can be in either the α or β configuration.

2. A 11-difluoromethylene steroid according to claim 1 where $R_6$ and $R_7$ are hydrogen atoms.

3. A 11-difluoromethylene steroid according to claim 1 where $R_{16}$ is a hydrogen atom.

4. A 11-difluoromethylene steroid according to claim 1 wherein $R_{18}$ is a methyl group.

5. A 11-difluoromethylene steroid according to claim 1 where $R_{18}$ is an ethyl group.

6. A 11-difluoromethylene steroid according to claim 1 which is selected from the group consisting of 11-difluoromethylene-estr-4-ene-3,17-dione and 11-difluoromethylene-13-ethylgon-4-ene-3,17-dione.

7. A $\Delta^4$-3-keto-17-substituted-11-difluoromethylene steroid of the formula

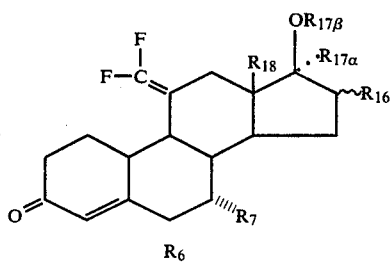

where
- $R_6$ is a hydrogen atom or methyl group with the proviso that when $R_6$ is a methyl group, $R_7$ is a hydrogen atom;
- $R_7$ is a hydrogen atom or methyl group with the proviso that when $R_7$ is a methyl group, $R_6$ is a hydrogen atom;
- $R_{16}$ is a hydrogen atom or methyl or ethyl group;
- $R_{17\alpha}$ is a hydrogen atom, alkyl of 1 thru 4 carbon atoms, —C≡C—$R_{17A}$ or —CH=CH—$R_{17B}$;
- $R_{17A}$ is a hydrogen atom, methyl or ethyl group or trifluoromethyl group;
- $R_{17B}$ is a hydrogen atom, methyl or ethyl group or —CH=$CH_2$ group;
- $R_{17\beta}$ is alkyl of 1 thru 4 carbon atoms and —CO—$R_{17C}$;
- $R_{17C}$ is alkyl of 1 through 6 carbon atoms, and phenyl;
- $R_{18}$ is a methyl or ethyl group; and
- $\sim$ indicates that the attached group can be in either the $\alpha$ or $\beta$ configuration.

8. A 17-substituted-11-difluoromethylene steroid according to claim 7 where $R_6$ and $R_7$ are hydrogen atoms.

9. A 17-substituted-11-difluoromethylene steroid according to claim 7 where $R_{16}$ is a hydrogen atom.

10. A 17-substituted-11-difluoromethylene steroid according to claim 7 where $R_{18}$ is a methyl group.

11. A 17-substituted-11-difluoromethylene steroid according to claim 7 where $R_{18}$ is an ethyl group.

12. A 17-substituted-11-difluoromethylene steroid according to claim 7 which is selected from the group consisting of 11-difluoromethylene-17β-hydroxy-17α-(1-propynyl)-estr-4-en-3-one and 11-difluoromethylene-13-ethyl-17β-hydroxy-17α-(1-propynyl)-gon-4-en-3-one.

13. A 17-substituted-11-difluoromethylene steroid according to claim 7 where $R_{17\alpha}$- is selected from the group consisting of ethynyl, propynyl, methyl and vinyl.

14. A 17-substituted-11-difluoromethylene steroid according to claim 7 where $R_{17\beta}$ is selected from the group consisting of hydrogen, methyl, ethyl and acetyl.

15. A $\Delta^4$-3-keto-17-substituted-11-difluoromethylene steroid according to claim 7 where $R_{17\beta}$ is a hydrogen atom giving a 17α-substituted-11-difluoromethylene steroid of the formula

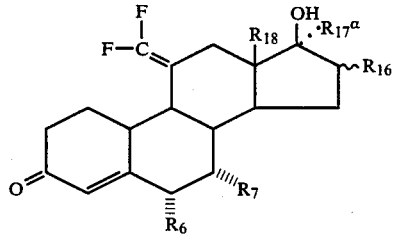

where $R_6$, $R_7$, $R_{16}$, $R_{17\alpha}$, $R_{18}$ and $\sim$ are defined in claim 7.

16. A $\Delta^4$-3-keto-17-substituted-11-difluoromethylene steroid according to claim 7 where $R_{17\beta}$ is alkyl of one thru 4 carbon atoms giving a ether of the formula

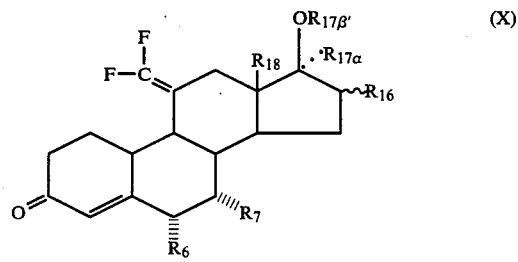

where $R_{17\beta'}$ is alkyl of 1 thru 4 carbon atoms and where $R_6$, $R_7$, $R_{16}$, $R_{17\alpha}$, $R_{18}$ and $\sim$ are defined in claim 7.

17. A $\Delta^4$-3-keto-17-substituted-11-difluoromethylene steroid according to claim 7 where $R_{17\beta}$ is —CO—$R_{17C}$ giving an ester of the formula

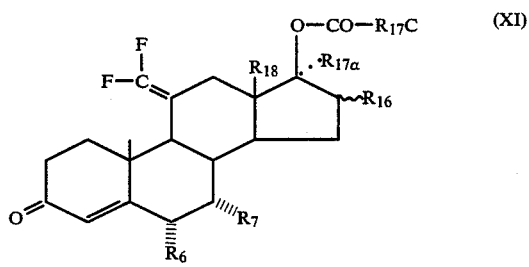

where
$R_{17C}$ is alkyl of 1 thru 6 carbon atoms, and phenyl and where $R_6$, $R_7$, $R_{16}$, $R_{17\alpha}$, $R_{18}$ and $\sim$ are defined in claim 7.

18. The syn- and anti-isomers of an oxime of the formula

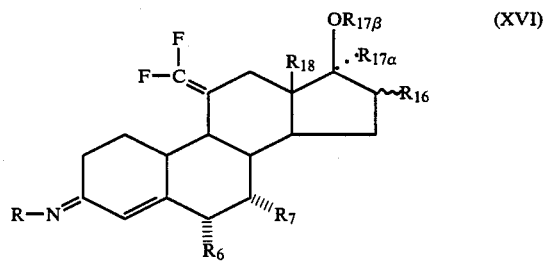

where
R is hydroxy or alkoxy where the alkyl group is from 1 thru 4 carbon atoms;

$R_6$ is hydrogen atom or methyl group with the proviso that when $R_6$ is a methyl group, $R_7$ is a hydrogen atom;

$R_7$ is a hydrogen atom or methyl group with the proviso that when $R_7$ is a methyl group, $R_6$ is a hydrogen atom;

$R_{16}$ is a hydrogen atom or methyl or ethyl group;

$R_{17A}$ is a hydrogen atom, methyl or ethyl group or trifluoromethyl group;

$R_{17\alpha}$ is a hydrogen atom, alkyl of 1 thru 4 carbon atoms, —C≡C—$R_{17}$A or —CH=CH—$R_{17}$B;

$R_{17B}$ is a hydrogen atom, methyl or ethyl group or —CH=CH$_2$ group;

$R_{17\beta}$ is alkyl of 1 thru 4 carbon atoms and —CO—$R_{17C}$;

$R_{17C}$ is alkyl of 1 through 6 carbon atoms, and phenyl; and $R_{18}$ is a methyl or ethyl group.

19. A 11-difluoromethylene steroid according to claim 18 where $R_6$ and $R_7$ are hydrogen atoms.

20. A 11-difluoromethylene steroid according to claim 18 where $R_{16}$ is a hydrogen atom.

21. A 11-difluoromethylene steroid according to claim 18 where $R_{18}$ is a methyl group.

22. A 11-difluoromethylene steroid according to claim 18 where $R_{18}$ is an ethyl group.

23. A 17-substituted-11-difluoromethylene steroid according to claim 18 where $R_{17\alpha}$- is selected from the group consisting of ethynyl, propynyl, methyl and vinyl.

24. A 17-substituted-11-difluoromethylene steroid according to claim 18 where $R_{17\beta}$ is selected from the group consisting of hydrogen, methyl, ethyl and acetyl.

* * * * *

UNITED STATES PATENT OFFICE
CERTIFICATE OF CORRECTION

Patent No. 4,567,000    Dated 28 January 1986

Inventor(s) D.E. Ayer

It is certified that error appears in the above-identified patent and that said Letters Patent are hereby corrected as shown below:

Column 1, line 38: "(11-" should read: --11- --.

Column 4, line 39: "by Reproduction" should read: --of Reproduction--.

Column 11, line 34: "053 g" should read: --0.53 g--.

Column 11, line 46: "13-ethylene-" should read: --13-ethylgon- --.

Signed and Sealed this

Thirteenth Day of May 1986

[SEAL]

Attest:

Attesting Officer

DONALD J. QUIGG

Commissioner of Patents and Trademarks